(12) United States Patent
Ergler et al.

(10) Patent No.: US 9,943,283 B2
(45) Date of Patent: Apr. 17, 2018

(54) CT SYSTEM HAVING A MODULAR X-RAY DETECTOR AND DATA TRANSMISSION SYSTEM FOR TRANSMITTING DETECTOR DATA

(71) Applicant: Siemens Aktiengesellschaft, Müchen (DE)

(72) Inventors: Thorsten Ergler, Erlangen (DE); Michael Hosemann, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 240 days.

(21) Appl. No.: 15/044,221

(22) Filed: Feb. 16, 2016

(65) Prior Publication Data

US 2016/0256129 A1    Sep. 8, 2016

(30) Foreign Application Priority Data

Mar. 3, 2015    (DE) .................. 10 2015 203 764

(51) Int. Cl.
*A61B 6/03* (2006.01)
*A61B 6/00* (2006.01)

(52) U.S. Cl.
CPC .............. *A61B 6/56* (2013.01); *A61B 6/032* (2013.01); *A61B 6/4266* (2013.01); *A61B 6/4411* (2013.01)

(58) Field of Classification Search
CPC ......... A61B 6/56; A61B 6/032; A61B 6/4411; G01N 2223/419; G01N 23/046
See application file for complete search history.

(56) References Cited

U.S. PATENT DOCUMENTS

| | | | |
|---|---|---|---|
| 6,823,039 B2 | 11/2004 | Hoheisel et al. | |
| 2003/0185338 A1* | 10/2003 | Dafni | A61B 6/032 378/15 |
| 2008/0272296 A1 | 11/2008 | Frach | |
| 2010/0063834 A1 | 3/2010 | Mukherjee | |

(Continued)

FOREIGN PATENT DOCUMENTS

| | | |
|---|---|---|
| CN | 103829968 A | 6/2014 |
| EP | 2733948 A1 | 5/2014 |

(Continued)

*Primary Examiner* — Don Wong
(74) *Attorney, Agent, or Firm* — Harness, Dickey & Pierce, P.L.C.

(57) ABSTRACT

A CT system is disclosed. In an embodiment, the CT system includes a stationary part, including a stationary part, including a plurality of non-rotating components; a rotatable part configured to rotate about a system axis during operation, including at least one x-ray detector, the at least one x-ray detector being modular in design and including a plurality of detector modules, the detector modules each including a plurality of detector pixels; a wireless data transmission system, to transmit at least detector information relating to a measured x-ray radiation from the rotatable part to the stationary part, the wireless data transmission system including at least one radio unit with a transmitter/receiver and at least one radio antenna, integrated in a plurality of the detector modules, to transmit at least the detector information; and at least one radio unit including a radio antenna and a receiver/transmitter, arranged on the stationary part.

25 Claims, 4 Drawing Sheets

(56) References Cited

U.S. PATENT DOCUMENTS

2012/0220875 A1    8/2012   Suri
2014/0093039 A1    4/2014   Yang et al.
2016/0156391 A1    6/2016   Fujii

FOREIGN PATENT DOCUMENTS

| | | |
|---|---|---|
| JP | 2002261641 A | 9/2002 |
| JP | 2014168520 A | 9/2014 |
| JP | 2014168521 A | 9/2014 |
| KR | 20140042321 A | 4/2014 |
| KR | 20150004287 A | 1/2015 |

* cited by examiner

CT SYSTEM HAVING A MODULAR X-RAY DETECTOR AND DATA TRANSMISSION SYSTEM FOR TRANSMITTING DETECTOR DATA

PRIORITY STATEMENT

The present application hereby claims priority under 35 U.S.C. § 119 to German patent application number DE 102015203764.9 filed Mar. 3, 2015, the entire contents of which are hereby incorporated herein by reference.

FIELD

At least one embodiment of the invention generally relates to a CT system. More preferably, it relates to a CT system with a stationary part, having a plurality of non-rotating components, and a part which rotates about a system axis during operation, having at least one x-ray detector, wherein the x-ray detector is modular in design and has a plurality of detector modules and wherein the detector modules each comprise a plurality of detector pixels, which preferably count x-ray photons impacting with a direct-converting sensor material in an energy-resolved manner, and furthermore with a wireless transmission system, with which at least detector information relating to a measured x-ray radiation is transmitted from the rotating part to the stationary part.

BACKGROUND

CT systems of the afore-cited type are generally known. It is also generally known that large quantities of data accumulate in the rotating part of a CT system, which have to be wirelessly transmitted to the stationary part, in particular, the detector data accumulating in one or in several detectors circulating the system axis of the CT system has to be transmitted quickly for evaluation purposes.

Currently data transmission typically takes place with the aid of slip ring systems, which develop a data transmission path via a capacitative coupling between the rotating part and the stationary part. The maximum capacitance of such slip ring systems is currently in the region of several 100 Mbit/s and is no longer sufficient here for the upcoming data transmission requirements of counting detectors, which have a significantly finer pixelation and moreover also have several energy thresholds per pixel, which again increase the data quantity to be transmitted.

It is basically also known to use radio transmission paths instead of slip ring systems for the transmission of the detector data between a rotating detector and a stationary part. However, the required data rates are not yet able to be achieved on their own.

SUMMARY

At least one embodiment of the invention includes a CT system, in which the high data quantities accumulating via counting detectors can be transmitted quickly.

Advantageous developments of the invention form the subject matter of the claims.

At least one embodiment of the invention includes a CT system, comprising:

a stationary part, including a plurality of non-rotating components;

a rotatable part configured to rotate about a system axis during operation, including at least one x-ray detector, the at least one x-ray detector being modular in design and including a plurality of detector modules, the detector modules each including a plurality of detector pixels;

a wireless data transmission system, to transmit at least detector information relating to a measured x-ray radiation from the rotatable part to the stationary part, the wireless data transmission system including at least one radio unit with a transmitter/receiver and at least one radio antenna, integrated in a plurality of the detector modules, to transmit at least the detector information; and at least one radio unit including a radio antenna and a receiver/transmitter, arranged on the stationary part.

BRIEF DESCRIPTION OF THE DRAWINGS

The invention is described below on the basis of example embodiments with the aid of the figures, wherein only the features required to understand the embodiments of the invention are shown. Here the following reference characters are used: 1: CT system; 2: x-ray tube; 3: x-ray detector; 3.0: sensor surface; 3.1: detector module; 3.2: scatter beam collimator; 3.3: radio unit; 3.4: transmit/receive unit; 3.5: ASIC; 3.5.1, 3.5.2: antenna; 3.6: sensor board; 3.7: radio unit; 4: patient; 5: measurement field; 6: housing; 6.1: gantry; 6.2: radio antennae; 6.3: antennae; 7: computer system; 8: patient couch; 9: system axis; Prg1-Prgn: programs.

Shown in detail are.

DETAILED DESCRIPTION OF THE EXAMPLE EMBODIMENTS

Figure 1:
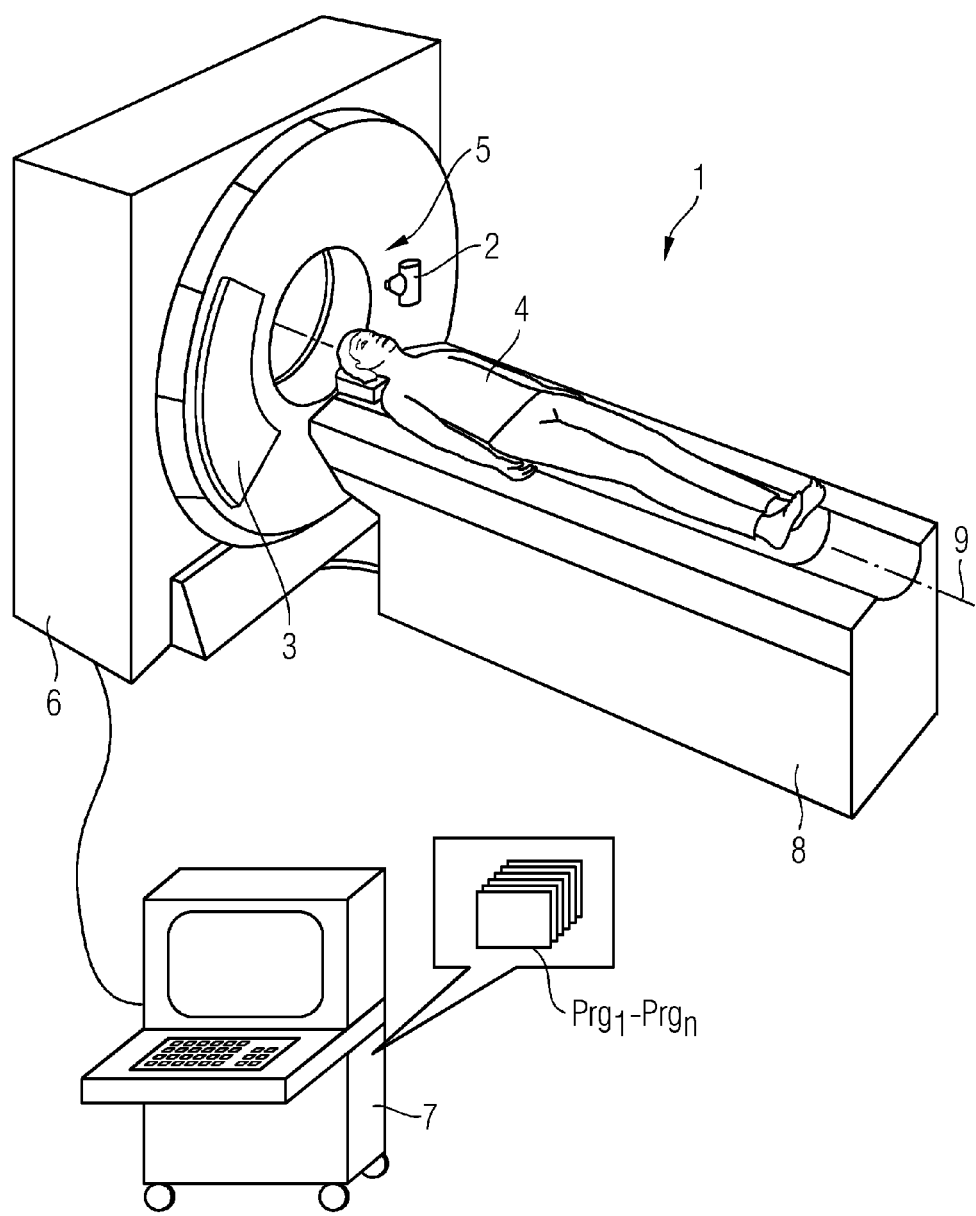
FIG. 1: Inventive CT system.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Further, although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

The inventors have recognized that with the x-ray detectors of a CT system generally already developed in a modular design with detector modules, a plurality of detector modules are to be immediately equipped with radio units, so that the detector data in the immediate vicinity of its site of development can transfer to a radio unit and the transmission can take place in a decentralized fashion by way of a number of radio units. It is particularly favorable here if each detector module has a separate radio unit, which is also integrated in the module electronics, so that the detector data developing in a detector module is immediately transferred to the respective radio unit present in this detector module and is sent without further intermediate steps and paths directly to the stationary part of the CT system. A transmission of the data via longer data transmission paths to a transmit unit is also avoided in this way.

In one possible development, provision can also be made for a number of radio units to exist per detector module, which can then be integrated for instance also into individual sensor boards, sensor modules or sensor module groups in order to transmit the detector data accumulating there immediately via radio transmission to a receive unit on the stationary part or stator of the CT system.

The inventive embodiment of the detector modules allows the radio transmission of the detector data to now be sent directly from each detector unit to the stationary part of the CT system. Instead of one individual antenna per detector unit, an antenna array can also be used here. The transmit characteristics can be adjusted with this depending on the detector position which can be determined for instance by an existing angular transmitter. Furthermore, one specific antenna can also be selected as a receive antenna depending on the position of the detector. Alternatively, all antennae on the detector modules can also be connected to form a larger antenna array and the selection of the receive characteristics can thus also take place depending on the detector position.

Moreover, the receive antennae can be attached to the stator in various arrangements, in order to reach optimal and/or alternating receive situations in each case. Examples of this are an annular arrangement outside of or inside of the rotation area of the detector or an arrangement as a group on the stator.

A further improvement in the data transmission between the rotor and the stator can be achieved in that the Doppler shift of the receive signal is corrected as a function of the angular position of the detector and its rotational speed.

While there is basically the possibility of operating the radio units on the detector modules with the same frequency, wherein a rotation angle-dependent time slot method can also be used here and/or in addition by the use of suitable antenna directional characteristics, e.g. a spatial alignment of the transmit and receive signal, the frequency resources can be used repeatedly, on the other hand radio units with different frequencies can also be operated at the same time in order to increase the data transmission rate.

Moreover, control data can be transmitted not only for the detector, but also for other components on the rotating part via one or a number of separate radio units, or is alternatively received by the static control unit by way of the radio units integrated into the detector modules.

The inventive embodiment of a CT system therefore allows for higher data transmission rates than were possible by way of a slip ring. No aggregation of the data of all modules is thus necessary and a simplified processing of the received detector data results, since these, corresponding to their assignment to the emitting detector module, each originate from afore-cited groups of pixels on the detector.

On account of the integration of the transmitter, the necessary components on the detector electronics reduce. The components for power supply, control and data readout, or data aggregation (signal backplane, module backplane), controller and various cables can be dispensed with or simplified for instance. Although additional transmit/receive units are conversely required, a reduction in the manufacturing outlay is however produced overall.

One significant advantage is also provided in that the radio transmission technology, contrary to slip ring technology, has a widespread use and accordingly also offers significantly more cost-effective components.

Based on a transmitting module unit, a simpler and detector electronics-independent scaling of the detector surface is also possible. To this end, adjustments only need to be made to the control unit on the static part of the system and the mechanics to hold the detector units. Moreover, the space requirements and also the climatic conditions are largely less complex than with slip ring technology.

According to these basic considerations, the inventors propose a CT system, comprising:
  a stationary part, having a plurality of non-rotating components,
  a part which rotates about a system axis during operation, having at least one x-ray detector,
  wherein the x-ray detector is modular in design and has a plurality of detector modules,
  wherein the detector modules each comprise a plurality of detector pixels and
  a wireless data transmission system, with which at least detector information relating to a measured x-ray radiation is transmitted from the rotating part to the stationary part.

An inventive improvement in the afore-cited CT system resides in at least one radio unit with a transmitter/receiver and at least one radio antenna for transmitting detector data being integrated into a plurality of detector modules and at least one radio unit with a radio antenna and a receiver/transmitter being arranged on the stationary part.

Each detector module can particularly advantageously be equipped with at least one radio unit. This embodiment then dispenses with the need to transmit, via detector module limits, the detector data to be sent to the preferably adjacent radio unit or radio units of an adjacent detector module.

In respect of an example embodiment of the radio unit, it is proposed that this at least one radio unit is arranged on a carrier ceramic for the sensor material in the form of an ASIC (application-specific integrated circuit). The radio unit is thus an integrated component of the detector module and requires at least very few to no separate external data connections. A reduction in the power supply connections is potentially also possible. Overall, an extremely compact design is thus enabled. With this feature, the respectively required antenna can also be generated directly on the carrier ceramic.

A plurality of radio antennae can advantageously be arranged on the stationary part, preferably directly on the stator, preferably opposite to the transmit antennae running past on the rotating part (rotor).

In many cases, e.g. for mechanical reasons, it is not possible to effect exactly identical angular distances for the antennae, so that deviations from the same angular distances of the antennae can be provided. This can basically be balanced out with information from the angle sensor. It is however particularly simple if such a compensation is not necessary and the radio antennae in the x-ray detector are arranged at the same angular distances in the direction of rotation of the rotor.

In particular, the radio antennae can be arranged on the stationary part at the same angular distances or 1/n-tel (integer fraction) of the angular distances of the radio antennae in the x-ray detector, wherein n is to be a whole number. If the transmit antennae in the x-ray detector are therefore arranged at an angular distance of 10°, the receive antennae are to be arranged on the stator likewise every 10° or every 5° or every 2.5°. This means that with the rotation at regular intervals, each antenna on the rotor faces an antenna on the stator and thus produces an optimal transmit/receive geometry. If a somewhat smaller cover is sufficient, the angular distances on the stator can also correspond to a whole number multiple of the angular distances on the rotor.

In one embodiment of the invention, it is proposed that all radio units are embodied to communicate on the same frequency. Alternatively, at least two radio units can also be embodied to communicate on different frequencies. The use of different frequencies within a frequency band easily allows the signals of different modules to be separated. Here different frequencies within a band can be assigned to different detector modules or module groups.

To avoid mutual crosstalk between the individual radio units, a time slot controller for transmit and receive times of the radio units can also be selected, wherein the time slots are to be triggered by the relative angular position of the rotating part in relation to the stationary part, since relatively low coordination outlay is required here. Alternatively, any known other variant of the time slot controller can however also be selected.

It was previously basically assumed that the transmit and receive antennae are disposed in each case on a peripheral line, preferably all in a plane at right angles to the axis of rotation of the rotor. In one particular embodiment, it is however also possible for at least two radio antennae offset in the system axis direction to be arranged per detector module. Accordingly, a set comprising several radio antennae can be arranged in each case at regular angular distances around the system axis on the stationary part in at least two different positions of the system axis (z-positions). The stationary angular positions of the radio antennae of the sets comprising a number of radio antennae on the stationary part can preferably be arranged here angularly offset in respect of one another.

With these embodiments, the antennae are therefore arranged in at least two different planes at right angles to the system axis therefore at least on the stationary part, if necessary also on the rotating part. There is the possibility here for the transmit and receive units to each comprise antennae, which are only assigned to one plane, or alternatively for a transmit and receive unit to each communicate with antennae from several planes. The subdivision can be optimized here in that the most favorable transmission output can be achieved on account of the existing environmental conditions or other built-in components.

Advantageously each detector module can also have at least one antenna array, with which a controller of the antenna directional characteristics is enabled, so that an optimal alignment of the transmit power is ensured at each transmit/receive time instant respectively. If such an array passes opposing receive antennae, which are present at 10° intervals, for instance, a precise alignment of the transmit lobe toward the next opposing receive antenna can take place in each case through a range of +/−5°, and can then be electronically aligned toward the next receive antenna while the previous receive antenna is taken over by the antenna array of the next radio unit on the detector. As a result, a continuous and almost interruption-free data transmission can be ensured between the detector and the stationary part with an antenna distance of 10° on the detector and 36 regularly arranged receive antennae on the stationary area.

On account of the relatively high rotational speeds of current CT systems, which result accordingly in Doppler effects on the communicating units, it may further be particularly advantageous if an apparatus for compensating for a Doppler shift in the radio transmission also exists between the radio units which are moved relative to one another during operation. Particularly with very high data rates, such Doppler effects can, on account of the varying timings in the bit streams, result in transmission errors, which can be compensated by the Doppler correction.

In a particular development of the CT system, it is also proposed that the radio units are to be embodied on the detector modules so as to transmit detector data exclusively. In addition to the radio units, at least one slip ring data transmission system can exist here, which primarily transmits control data between the stationary and the rotating part.

Alternatively and preferably, at least one radio unit can however be embodied on at least one detector module in the inventive CT system, so as to also transmit control data in addition to the detector data. It is certainly more favorable if at least one additional radio unit exists, which is embodied to exclusively transmit non detector data, preferably exclusively control data for the rotating part without detector data.

The use of the predescribed radio transmission in conjunction with counting detectors is particularly advantageous, since on the one hand the pixelation is on the whole finer here than with integrating detectors. In addition, the quantity of data to be transmitted increases again on account of the energy-resolved photon count, which results in a duplication of the data per pixel and measuring point.

FIG. 1 shows an inventive embodiment of a CT system 1 with a housing 6, in which significant parts of the stationary part of the CT system and also the rotating part of the CT system are disposed. At least one emitter-detector system including the x-ray detector 3 in modular design and the opposing x-ray tube 2 is essentially disposed on the rotating part, in other words the gantry of the CT system. Alternatively, a number of emitter-detector-systems can also be arranged on such a gantry. The gantry (not shown in more detail here) surrounds an opening in the housing 6, in which during operation the measurement field 5 of the active emitter-detector systems is formed.

For measurement purposes the patient 4, who is located on a patient couch 8 which can be moved in the direction of the system axis 9, is moved through the measurement field continuously or in stages, while the detector 3 and the x-ray tube rotate about the system axis 9. Here the attenuation of the x-ray radiation emitted by the x-ray tube is measured pixel by pixel by the patient 4, wherein direct-converting sensor materials are preferably used and the impacting x-ray photons are counted in an energy-resolved manner.

In accordance with an embodiment of the invention, the detector data determined in the process is wirelessly send via radio units integrated in the detector via radio, in other words by high-frequency electromagnetic radiation, to the stationary part of the CT system. The control of the overall CT system 1 and also the evaluation of the received measurement data takes place by way of a computer system 7, with the aid of the programs Prg1-Prgn stored there and executed during operation.

Figure 2:
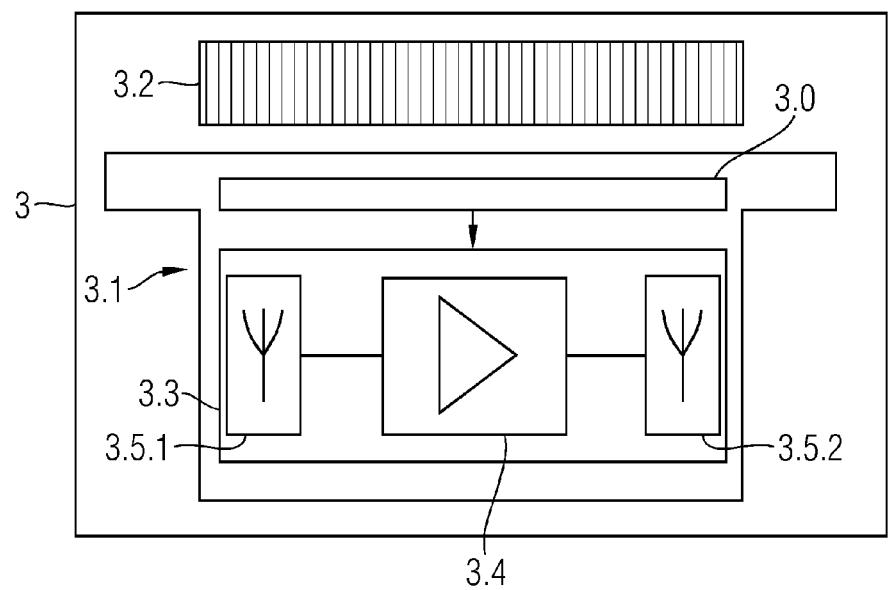
FIG. 2: Detector module with integrated radio unit.

FIG. 2 shows by way of example a cross-section through a detector 3 with the scattered beam collimator 3.2 arranged above, the detector module 3.1 with a sensor surface 3.0 and the radio unit 3.3 integrated in the detector module 3.1 including of a transmit/receive unit 3.4 and two antennae 3.5.1 and 3.5.2 arranged laterally in the system axis direction. The antennae shown here can on the one hand be operated separately with predefined antenna characteristics, but can also be used as part of an antenna array, in which the directional characteristics are influenced by corresponding phase control.

Figure 3:
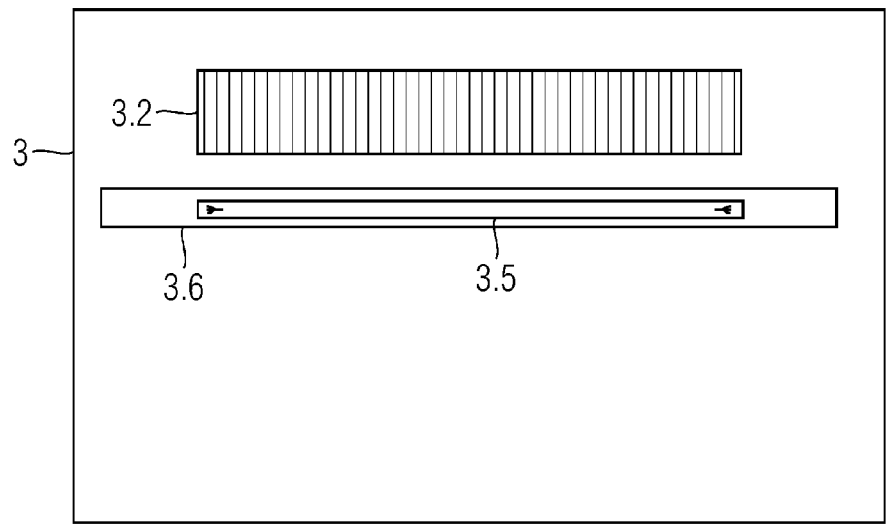
FIG. 3: Sensor board of a detector module having an integrated radio ASIC.

Alternatively, the radio units from FIG. 2 can also be immediately embodied on the carrier ceramics of the sensor board 3.6 as ASIC 3.5, as shown in FIG. 3.

FIGS. 4 to 7 now show different inventive embodiment variants of the antenna arrangement on the basis of cross-sections through a schematically shown housing 6 of a CT system with a detector 3 shown by way of example.

Figure 4:
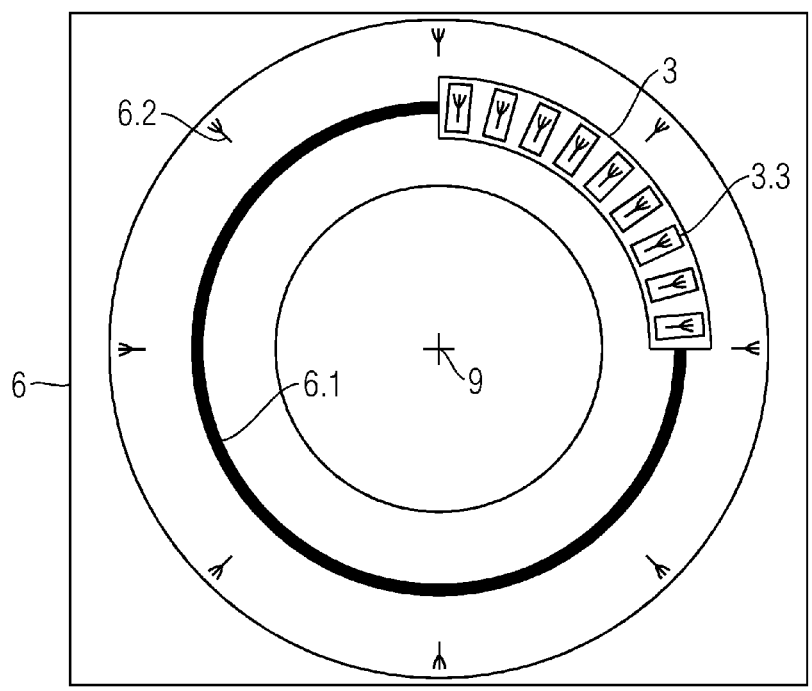
FIG. 4: cross-section through the gantry of a CT system with radio units integrated in the detector and radio antennae on the stator arranged outside of the gantry.

FIG. 4 shows a cross-section through the gantry 6.1 of a CT system with radio units 3.3 integrated in the detector 3 and radio antennae 6.2 on the stationary part of the CT system arranged outside of the turning radius of the gantry 6.1. In the example shown, eight antennae 6.2 with an angular offset of 45° are arranged, so that the detector and thus also each antenna in the radio units pass an antenna eight times during a revolution in each case and gains the opportunity to transmit the detector data.

Figure 5:
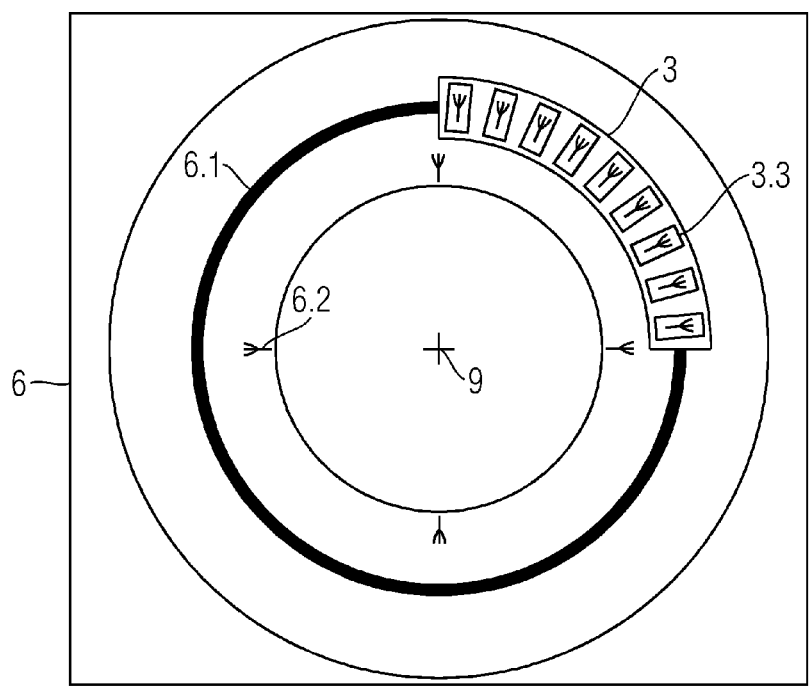
FIG. 5: cross-section through the gantry of a CT system with radio units integrated in the detector and radio antennae on the stator arranged within the gantry.

An alternative variant is apparent in FIG. 5. Four stationary antennae are arranged here within the turning circle of the gantry 6.1. With such an embodiment, it may be particularly advantageous if instead of simple antennae on the detector side, antenna arrays are used, which then align their transmit lobe, irrespective of their position, toward an antenna of the stationary part which is available in each case.

Figure 6:
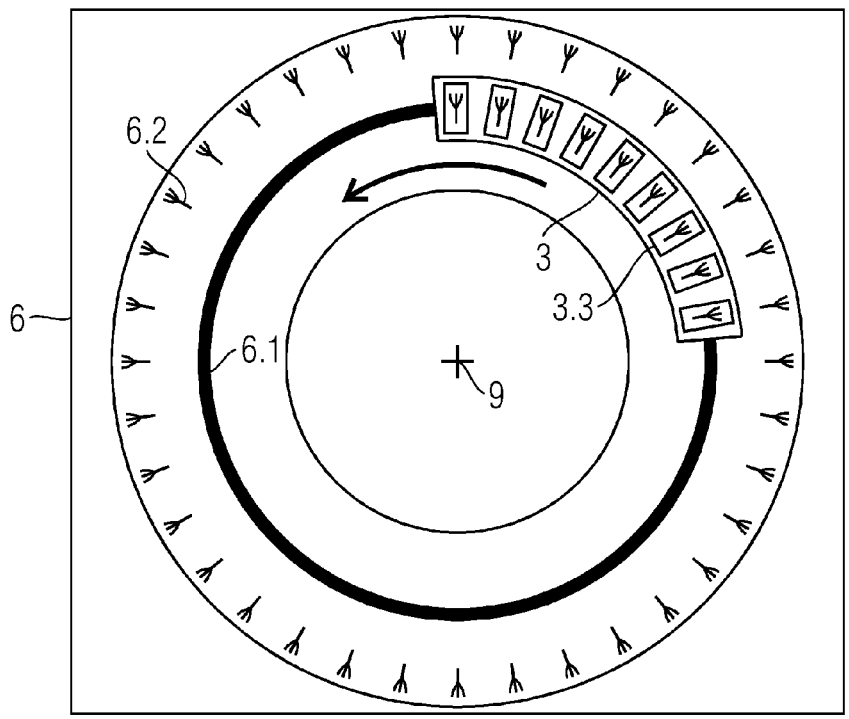
FIG. 6: cross-section through the gantry of a CT system with radio units integrated in the detector and radio antennae on the stator arranged outside of the turning circle of the gantry with the same angular distance as in the detector.

One embodiment with potential for significantly higher data transmission rates is shown in FIG. 6. Antennae, which have the same angular distance of 10° relative to one another, such as the antennae in the radio units 3.3 on the detector modules of the detector 3, are disposed here in the peripheral region 36. An antenna 6.2 is also disposed here on the stationary part in the transmit-receive area at any time that the detector circulates about the system axis 9 for each antenna in the detector 3. Accordingly, detector data with very high data rates can be transmitted almost continuously during the rotation of the detector. In this embodiment, the control data can either be transmitted in addition to the detector data on the same transmission paths, or a separate transmission path can be selected by way of a slip ring system.

Figure 7:
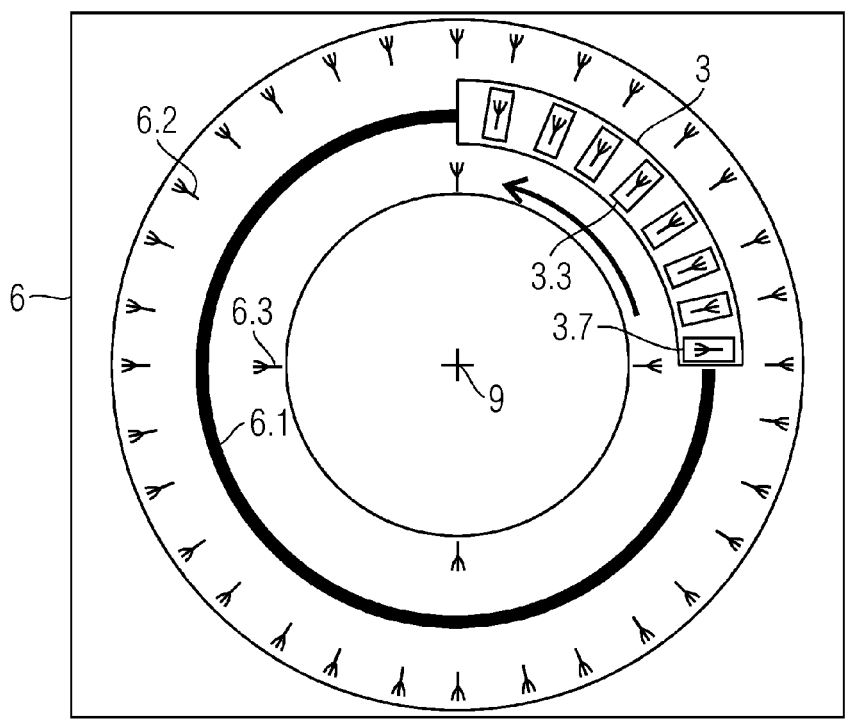
FIG. 7: cross-section through the gantry of a CT system with radio units integrated in the detector and radio antennae on the stator arranged outside of the turning circle of the gantry with the same angular distance as in the detector and additional radio unit for transmitting control data.

Another variant of the antenna arrangement is shown in FIG. 7, which, in respect of the antennae for the detector data transmission, is embodied like FIG. 6. However, another additional radio unit 3.7 is also arranged in the detector 3, said radio unit being aligned to the inner circle of the antennae 6.3. In this embodiment variant, the detector data can thus be exclusively transmitted via the radio units 3.3 to the outer antennae 6.2, while the control commands are exclusively transmitted via the additional radio unit 3.7 arranged in the detector to the inner circle of the antennae 6.3.

Overall, an embodiment of the invention presents a CT system, which, by integrating radio units on the detector modules for the decentralized and parallel transmission of the detector data, allows for a very high overall data transmission rate, removes superfluous data which is not required and also reduces the complexity of the rotating part by omitting internal data connections between the detector modules and central data transmission systems.

An embodiment of the invention is generally described accordingly by a CT system, in which at least one radio unit with a transmitter/receiver and at least one radio antenna for transmitting detector data are integrated into a plurality of detector modules in each case while at least one radio unit with a radio antenna and a receiver/transmitter are arranged on a stationary part. Within the scope of embodiments of the invention, it is also natural to combine such a CT system with individual or a number of further embodiment features cited in this application.

Although the invention has been illustrated and described in greater detail by the example embodiment, the invention is not limited by the examples disclosed and the person skilled in the art will be able to derive other variations on this basis without departing from the scope of protection of the invention.

The aforementioned description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods. Further, elements and/or features of different example embodiments may be combined with each other and/or substituted for each other within the scope of this disclosure and appended claims.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Further, at least one embodiment of the invention relates to a non-transitory computer-readable storage medium comprising electronically readable control information stored thereon, configured in such that when the storage medium is used in a controller of a magnetic resonance device, at least one embodiment of the method is carried out.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A CT system, comprising:
   a stationary part, including a plurality of non-rotating components;
   a rotatable part configured to rotate about a system axis during operation, including at least one x-ray detector, the at least one x-ray detector being modular in design and including a plurality of detector modules, the detector modules each including a plurality of detector pixels;
   a wireless data transmission system, to transmit at least detector information relating to a measured x-ray radiation from the rotatable part to the stationary part, the wireless data transmission system including at least one radio unit with a transmitter/receiver and at least one radio antenna, integrated in a plurality of the detector modules, to transmit at least the detector information; and
   at least one radio unit including a radio antenna and a receiver/transmitter, arranged on the stationary part.

2. The CT system of claim 1, wherein each of the plurality of detector modules is equipped with at least one radio unit.

3. The CT system of claim 1, wherein the radio unit is arranged on a carrier ceramics for the sensor material in the form of an ASIC.

4. The CT system of claim 1, wherein a plurality of radio antennae are arranged on the stationary part.

5. The CT system of claim 1, wherein the radio antennae are arranged in the x-ray detector at equal angular intervals in the direction of rotation.

6. The CT system of claim 4, wherein the radio antennae on the stationary part are arranged at the same angular distances or an integer multiple or an integer fraction of the angular intervals of the radio antennae in the x-ray detector.

7. The CT system of claim 2, wherein all radio units are embodied for communication at a common frequency.

8. The CT system of claim 2, wherein at least two radio units are embodied for communication at different frequencies.

9. The CT system of claim 2, further comprising:
   a time slot controller to transmit and receive times of the radio units, wherein the time slot is triggered by the relative angular position of the rotating part in relation to the stationary part.

10. The CT system of claim 1, wherein at least two radio antennae, offset in the system axis direction, are provided per detector module.

11. The CT system of claim 1, wherein a set of several radio antennae are arranged at regular angular intervals about the system axis on the stationary part in at least two different positions of the system axis.

12. The CT system of claim 11, wherein the stationary angular positions of the radio antennae of the sets comprising a number of radio antennae are arranged angularly offset relative to one another on the stationary part.

13. The CT system of claim 1, wherein at least one antenna array with a controller of the antenna directional characteristics exists per detector module.

14. The CT system of claim 1, wherein an apparatus to compensate for a Doppler shift in the radio transmission exists between the antennae moved relative to one another during operation.

15. The CT system of claim 1, wherein the at least one radio unit includes a plurality of radio units, and wherein the plurality of radio units on the detector modules are embodied exclusively to transmit detector data.

16. The CT system of claim 15, further comprising:
   at least one slip ring data transmission system, to primarily transmit control data between the stationary and the rotatable part.

17. The CT system of claim 1, wherein the at least detector information includes control data and detector data, at least one radio unit being embodied on at least one detector module to transmit the control data in addition to the detector data.

18. The CT system of claim 1, wherein the at least detector information includes non-detector data and detector data, the CT system further comprising:
   at least one additional radio unit, embodied to exclusively transmit non-detector data, preferably exclusively control data, for the rotating part.

19. The CT system of claim 1, wherein the detector is equipped with a direct-converting sensor material, to count impacting x-ray photons, pixel by pixel, in an energy-resolved manner during operation.

20. The CT system of claim 1, wherein the at least one radio unit integrated in a plurality of the detector modules includes a plurality of radio units, and wherein all of the radio units are embodied for communication at a common frequency.

21. The CT system of claim 1, wherein the at least one radio unit integrated in a plurality of the detector modules includes a plurality of radio units, and wherein at least two of the radio units are embodied for communication at different frequencies.

22. The CT system of claim 1, wherein the at least one radio unit integrated in a plurality of the detector modules includes a plurality of radio units, the CT system further comprising:
- a time slot controller to transmit and receive times of the plurality of radio units, wherein the time slot is triggered by the relative angular position of the rotating part in relation to the stationary part.

23. The CT system of claim 2, wherein a set of several radio antennae are arranged at regular angular intervals about the system axis on the stationary part in at least two different positions of the system axis.

24. The CT system of claim 23, wherein the stationary angular positions of the radio antennae of the sets comprising a number of radio antennae are arranged angularly offset relative to one another on the stationary part.

25. The CT system of claim 1, wherein the non-detector data includes control data, the CT system further comprising:
- at least one additional radio unit, embodied to exclusively transmit control data for the rotating part.

* * * * *